United States Patent [19]

Maier

[11] Patent Number: 5,056,370

[45] Date of Patent: Oct. 15, 1991

[54] METHOD AND APPARATUS FOR TESTING A TEST PIECE

[76] Inventor: Wolfgang Maier, Berliner Strasse 111, 3300 Braunschweig, Fed. Rep. of Germany

[21] Appl. No.: 554,346

[22] Filed: Jul. 19, 1990

[51] Int. Cl.$^5$ .............................................. G01N 3/00
[52] U.S. Cl. ...................................................... 73/794
[58] Field of Search .................................. 73/794, 795

[56] References Cited

U.S. PATENT DOCUMENTS 2,446,566  8/1948  Wenk ....................................... 73/88

FOREIGN PATENT DOCUMENTS 3425359  12/1986  Fed. Rep. of Germany .

OTHER PUBLICATIONS

Maier, "The B.T.M. Testing System Applications for Six Degree Freedom of Condition Loading", Institute of Steel Construction Technology University of Braunschweig, 1988.
Maier et al., "The BTM-Concept-An Experimental Method to Simulate the Behavior of Substructures Consisting of Truss or Beam Members", pp. 1-6, published 1988, at the Ninth World Conference on Earthquake Engineering.
"Multi-Degree of Freedom Boundary Condition Simulator", MTS Design Description, 1988.
Kiel, "Development of an Intelligent Testing Machine for Complete Supporting Structures Exposed to Fire", presented at the Braunschweig Fire Protection Conference 1989, Sep. 6 and 7.
Ramu et al., "Experimental Installation for the Testing of Supports Under Permanent Loads", Schweizer Archiv., vol. 34, No. 9, pp. 273-282, published Sep. 1968.
Maier, "The Concept of Communicating Experimental Methods for Supporting Girder Structures", pp. 141-147, University of Stuttgart, Germany, 1986.

*Primary Examiner*—Robert Raevis
*Attorney, Agent, or Firm*—Foley & Lardner

[57] ABSTRACT

A method and apparatus for testing a test piece having opposing ends includes connecting the ends of the test piece to a first load head and to a plate which may be attached to a second test head, respectively. The device actuates a driving device to spatially adjust the load head to apply a variable load to the test piece. The device determines the magnitude and direction of load head displacement variables applied to the load head, measures the actual magnitude and direction of displacement of the load head in relation to a fixed plate, sets and varies boundary conditions of the test piece from the displacement of the load head, compares actual values of the boundary conditions with freely programmable predetermined desired values of the boundary conditions, and determines a control variable for the driving device. In order to extend testing capabilities, the device determines additional control variables for the driving device using one of values measured in a test area located between the ends of the test piece and values that can be reduced to correspondingly measured values, wherein functional dependencies of the additional control variables are determined before the determination of the load head displacement variables or by identifying the additional control variables in the test.

22 Claims, 9 Drawing Sheets

METHOD AND APPARATUS FOR TESTING A TEST PIECE

BACKGROUND OF THE INVENTION

The invention relates to a method of testing a test piece, in particular in bar form, the one end of which is connected to a plate and the opposite end of which is connected to a first load head, which can be spatially adjusted as desired by a driving means. In this method, load variables applied to the load head are determined in absolute amounts, and the direction and the spatial displacement of the load head is measured in relation to a fixed plate, so that the boundary conditions of the test piece can be specifically set and varied by the displacement of the load head. By comparison of the actual values with freely programmable predetermined desired values of the boundary conditions or limiting conditions, a testpiece end value in the form of a displacement variable and/or force variable can be determined as a control variable for the driving means.

An example of this method is disclosed in German Patent Specification No. 3,425,359; the subject matter of which is incorporated by reference. The test apparatus used for the disclosed method substantially comprises a test frame with at least one abutment arrangement for supporting the forces acting on the component under test, at least one load head, which is displaceably connected to a driving means and the bearing surface of which could be rigidly connected to the component for introducing loads into the latter, as well as measuring means for determining the force variables applied by the driving means to the load head. In this method, the only way in which the boundary conditions of the component can be varied before and during the test without exchanging the load head is by the spatial displacement of the latter for any number of degrees of freedom. The force variables can be determined vectorially and for a preselected number of degrees of freedom by the measuring means. Further measuring means for determining the spatial displacement of the bearing surface with respect to the opposite abutment arrangement are built-in. For displacing the load head, a controlling means is provided, in which a control variable for the driving means can be derived in a process computer from the measured values determined by the measuring means and the preselected desired values of the boundary conditions. In this case, a longitudinally displaceable loading pendulum, which is articulated by one end to the test frame and by the other end to the load head, is provided as driving means for each degree of freedom. These loading pendulums may be designed as hydraulic piston-cylinder arrangements with admission possible at both ends. The load head itself may be designed as a plate arrangement, the loading pendulums being articulated on its edge regions. For vectorial determination of the force variables applied to the load head, two force sensors are provided, arranged axially apart, on each loading pendulum for the measurement of the normal forces and bending moments in two cross-sections of the loading pendulum. A displacement sensor is also provided.

With this known test apparatus, all of the load-dependent boundary conditions can be set or varied in a defined manner before and during the test without exchanging the load head. Something which is essential for the test apparatus is the rigid connection between the test piece and the load head, irrespective of the boundary conditions chosen. The component must therefore be firmly connected to the load head at its sectional surface. The boundary conditions of the test piece are influenced by the movement of the load head and consequently can be specifically set and varied. By comparison of the actual values and desired values of the boundary conditions, the control variable can be determined for the driving means. Consequently, even in the case of a nonlinear relationship between force variables and displacement variables, all stress resultants that are structure-mechanically compatible with the component, that is to say force variables and displacement variables and consequently all boundary conditions, can be applied by step-by-step displacement of the load head, with the result that a determination of the bearing behavior of the component in dependence on the preselected boundary conditions is possible.

Thus, with the known test apparatus, it is intended for any boundary conditions of the bar-shaped test piece to be set. Therefore, the control variables are bar end values, to be precise bar end displacement variables, bar end force variables or generally a combination of these variables. The load plate with the bar-shaped test piece connected thereto consequently has to be assumed to be rigid and actually must be sufficiently stiff up to the (theoretical) end of the bar, i.e. including the fastening construction.

SUMMARY OF THE INVENTION

The invention is based on the object of refining the above-described method in such a way that the transitional region between the end of the test piece and the load plate no longer has to be made sufficiently rigid for control using bar end values as the only control variables, in order that, with non-rigid connecting regions, values other than bar end values can be included in the control.

In accordance with a first aspect of the invention, a method of testing a test piece having opposing ends includes the steps of connecting one end of the test piece to a plate of a test apparatus, connecting the opposite end of the test piece to a first load head of the test apparatus, and actuating driving means to spatially adjust the load head, thereby applying a variable load to the test piece. Additional steps include determining the magnitude and direction of load head displacement variables applied to the load head and measuring the actual magnitude and direction of displacement of the load head in relation to the fixed plate, and setting and varying boundary conditions of the test piece from the displacement of the load head. Other steps include comparing actual values of the boundary conditions with freely programmable predetermined desired values of the boundary conditions to determine, as a control variable for the driving means, a test piece end value in the form of at least one of a displacement variable and a force variable. Another step comprises determining additional control variables for the driving means using one of values measured in a test area located between the ends of the test piece and values that can be reduced to correspondingly measured values, wherein functional dependencies of the additional control variables are determined before the test or by identifying the additional control variables in the test.

In accordance with another aspect of the invention, the step of connecting one end of the test piece to a plate comprises the step of connecting the one end to a second displaceable load head.

In accordance with another aspect of the invention, the step of determining additional control variables comprises the steps of imposing forces on the test area, measuring the imposed forces, and deriving the additional control variables from the measured force values. The imposed forces may be transmitted away from the test apparatus, onto load plates, or onto the test frame.

In accordance with yet another aspect of the invention, the step of determining additional control variables is performed using values derived from measured values of forces taken away from the test area. The imposed forces may be transmitted away from the test apparatus, onto load plates, or onto the test frame.

Another object of the invention is to provide an apparatus for testing a test piece having two opposed ends.

In accordance with one aspect of the invention, the apparatus includes a test frame, a plate supported on the test frame and connected to one end of the test piece, a first load head supported on the frame and connected to the opposite end of the test piece, and driving means for spatially adjusting the load head, thereby applying a variable load to the test piece. Also included are means for determining the magnitude and direction of load head displacement variables applied to the load head and for measuring the actual magnitude and direction of displacement of the load head in relation to a fixed plate, and for setting and varying boundary conditions of the test piece from the displacement of the load head. Further means compare actual values of the boundary conditions with freely programmable predetermined desired values of the boundary conditions to determine a test piece end value in the form of at least one of a displacement variable and a force variable, and actuate the driving means using the determined test piece end value as a control variable. Also included are means for determining additional control variables for the driving means using one of values measured in a test area located between the ends of the test piece and values that can be reduced to correspondingly measured values, wherein the functional dependencies of the additional control variables are determined before the test or by identifying the additional control variables in the test.

In accordance with another aspect of the invention, the apparatus includes a second displaceable load head positioned between the plate and the test frame.

Other objects, features and advantages of the present invention will become apparent to those skilled in the art from the following detailed description. It should be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

A number of illustrative embodiments of the invention, serving as examples, are diagrammatically represented in the drawings, in which.

DETAILED DESCRIPTION OF THE PREFERRED EMBODIMENTS

Figure 9:
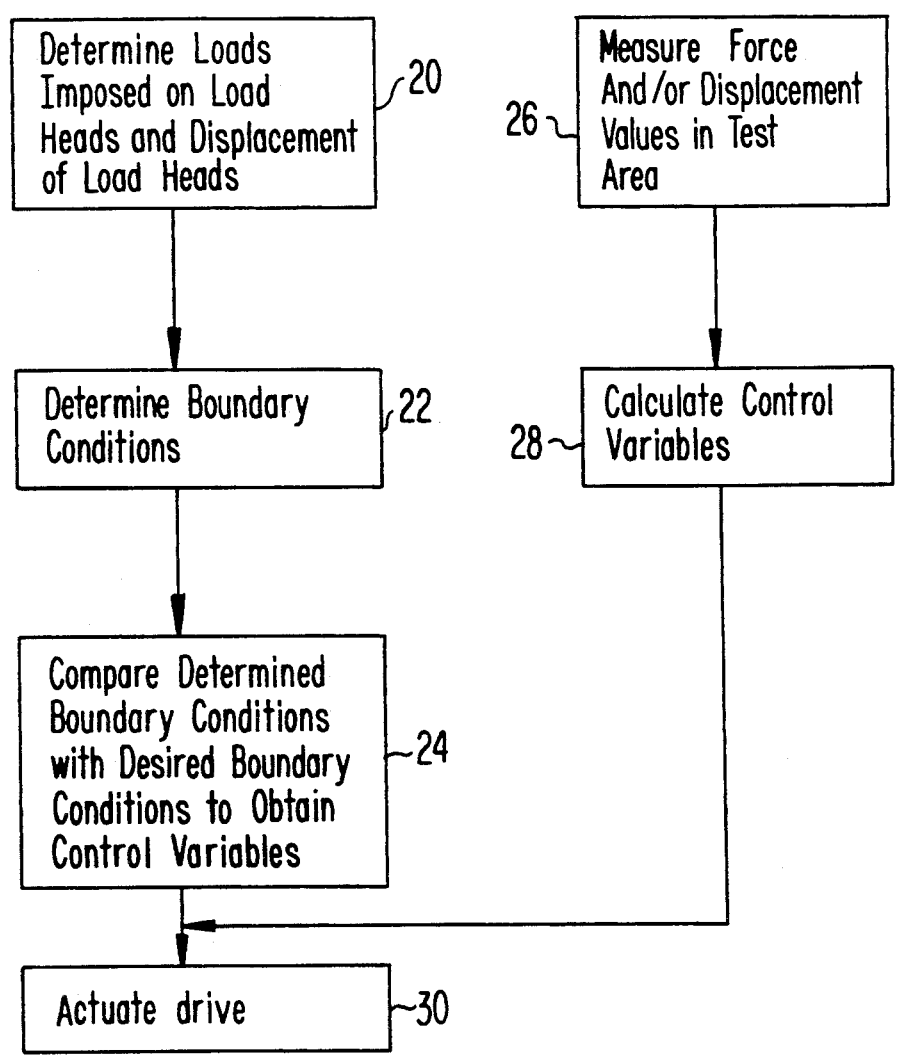
FIG. 9 illustrates the operation of the devices of FIGS. 1-8.

In each of the embodiments discussed below, one end of a test object is connected to a plate, and the opposite end is connected to a first load head, which can be spatially adjusted as desired by a suitable driving means. Referring to FIG. 9, absolute loads applied to the load head by the driving means are determined in a suitable control means, e.g. a micro-processor or a process computer 12, and the direction and magnitude of spacial displacement of the load head is measured in relation to a fixed member at step 20, so that the boundary conditions of the test piece can be determined specifically set and varied by the displacement of the load head at step 22. The actual values of the boundary condition are compared at step 24, e.g., by a comparator, with freely programmable predetermined desired values of the boundary conditions. As a result of this comparison, a test-piece end value in the form of a displacement variable and/or a force variable can be determined as control variables for actuating the driving means.

In order to use control variables for the driving means other than the values of forces acting on the ends of the test object, measured values are used, which are measured in a test area located between the ends of the test piece, or are mathematically reduced to correspondingly measured values from measurements taken outside of the test area at step 26. The measured values are also used as control variables for the driving means at step 28. The functional dependencies of these additional control variables with respect to the determined load head displacement variables are formulated in advance by the control means. The control means actuates the drive in a manner which is per se well known at step 30.

At the same time, it is expedient if the one end of the test piece is connected to a displaceable second load head.

The measured values used for the additional control variables may be derived by the control means from forces imposed in the test area. These forces may be measured by sensors cooperating with the two load heads are together designed with at least six degrees of freedom.

However, there is also the possibility of deriving the measured values used for the additional control variables from forces taken from the area under investigation. In this case, it is expedient if the two load heads are each provided with six degrees of freedom.

The supporting force measurement may be performed directly or via a load head.

In the testing of test pieces having more than two ends, it is expedient if each piece end is assigned a separate load head.

Figure 1:
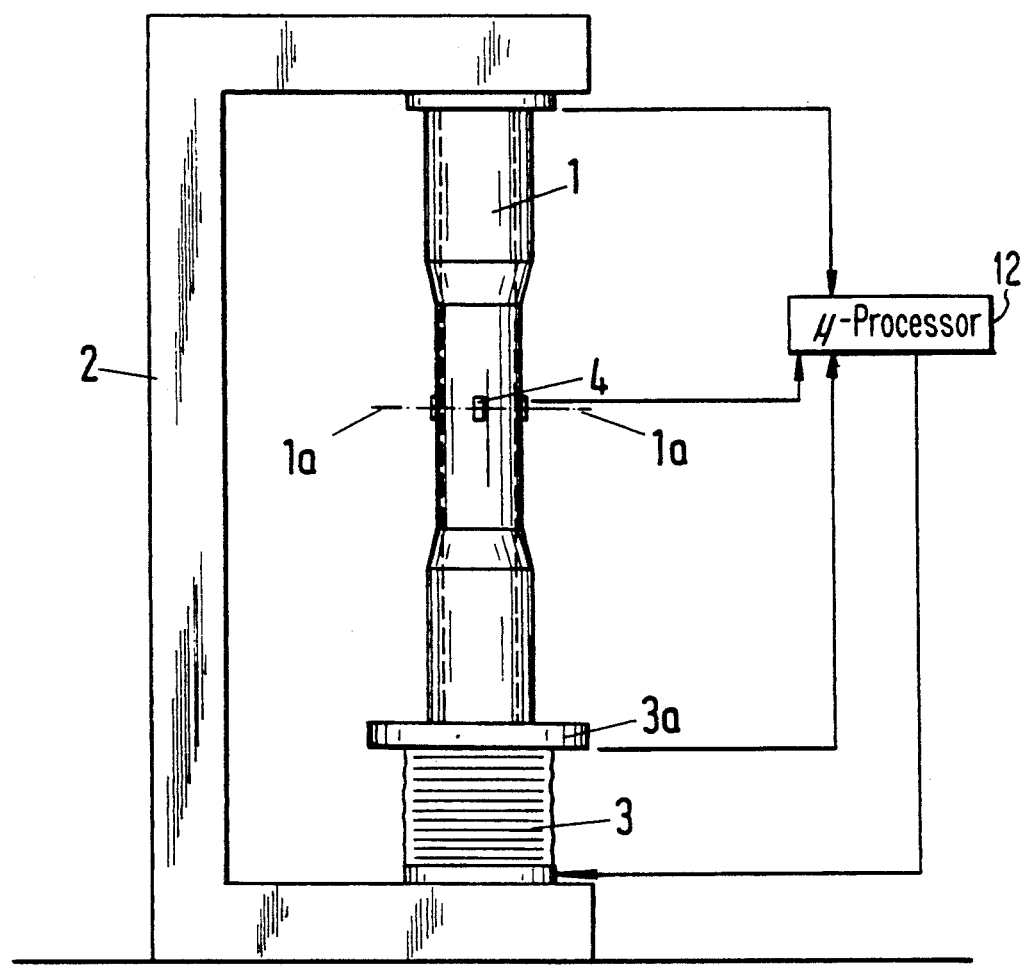
FIG. 1 shows a first embodiment of the invention including a tube specimen in a test apparatus with a load head.

FIG. 1 shows, as a test piece 1, a tube specimen, which is restrained in a test frame 2. The test area of the tube specimen is denoted by 1a and is small in comparison with the test piece 1. The tube specimen is subjected to a cyclic stress by a normal force and a torsional moment to investigate the material behavior in the plastic range. For control variables, the change in length and the torsion angle of the area under investigation are used. These control variables are measured with a measuring strip 4 and are substituted for the boundary conditions constituting vertical displacement and the torsional twisting at the upper end of the bar. A driven displaceable load head 3 with a load plate 3a is provided at the lower end of the bar. As further control variables, boundary conditions comprising the two horizontal displacements and the two bending moments at the upper end of the bar as well as six displacement variables at the lower end of the bar are used.

Figure 2:
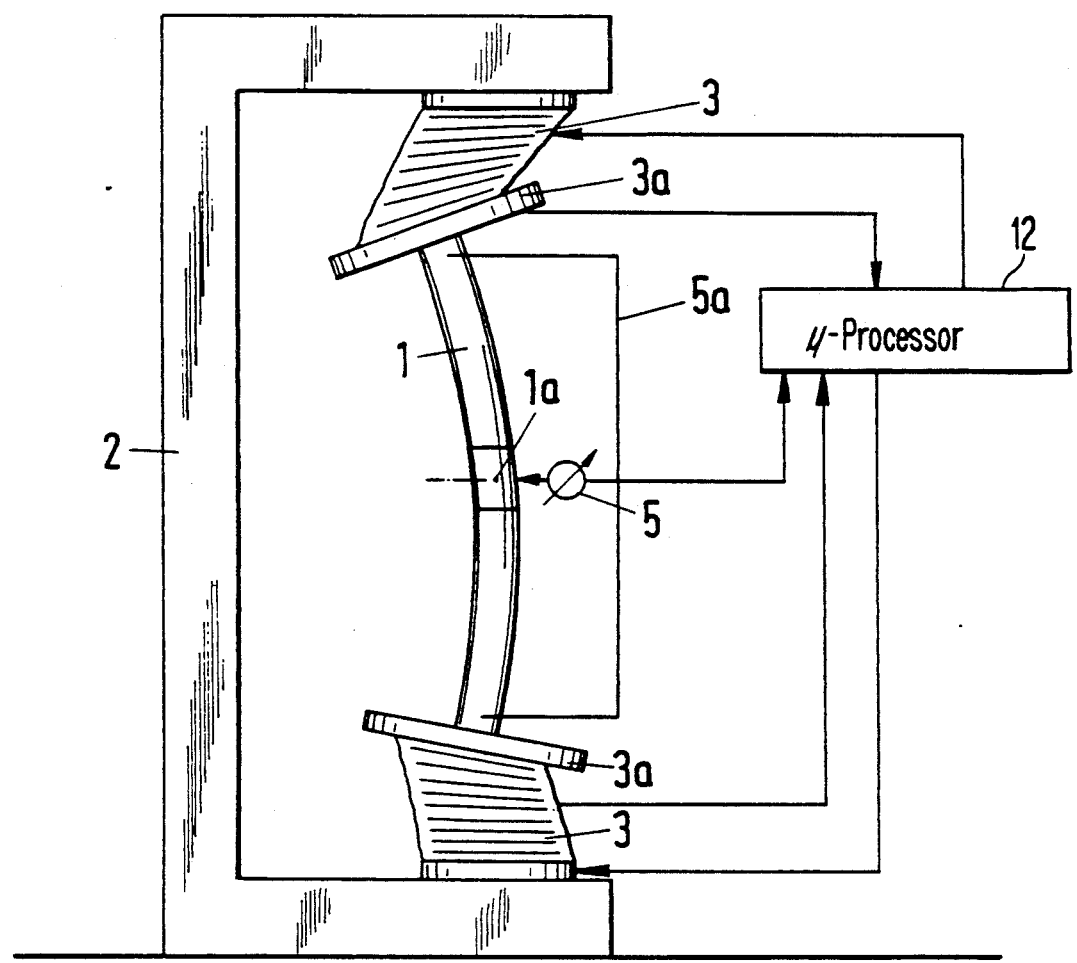
FIG. 2 shows a second embodiment of the invention including a bar-shaped test piece in a test apparatus with two load heads.

FIG. 2 shows a bar-shaped test piece 1 which is restrained between a lower driven displaceable load head 3 with a load plate 3a and an upper driven displaceable load head 3 with a load plate 3a. Under the action of an eccentric tensile force imposed by a known force transmitting means—with constant eccentricity in the area of impact 1a—the assembly experiences a horizontal displacement. The additional control variable is the eccentricity of the normal force in the area of impact 1a, measured with a displacement sensor 5 mounted on a holder 5a, and transmitted to the control means.

With constant eccentricity at the end of the bar, the eccentricity would be reduced in the area of impact 1a. With a control exclusively by means of bar end values, i.e., by applying force exclusively to the end of the bar, a constant eccentricity at the end of the bar would result, for example, from the control variable of normal force imposed on the end of the bar N and the control condition $M = c \times N$, M being the bending moment at the end of the bar and c being the desired eccentricity. For a constant eccentricity in the area of impact 1a, all that is necessary is to substitute the control condition by $M = (c+e) \times N$, e being the the eccentricity of the bar at point 1a from the vertical control the lead of the bar.

Figure 3:
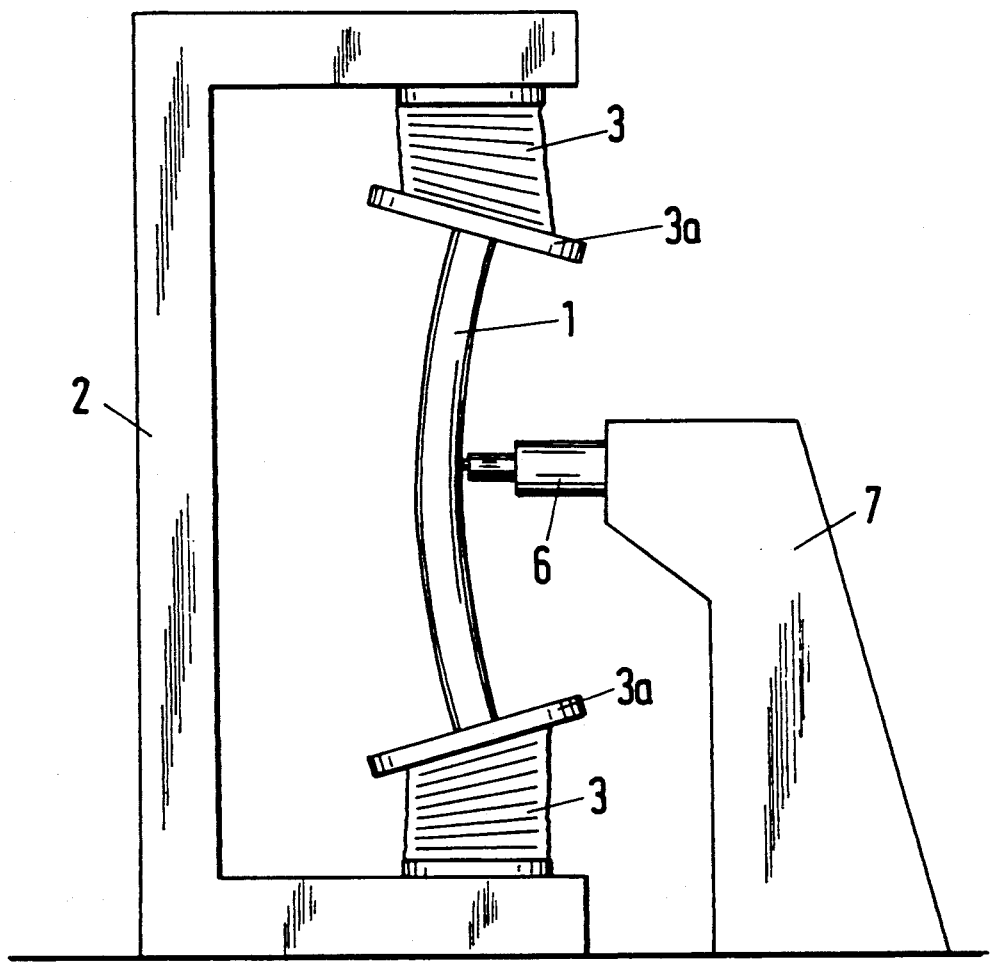
FIGS. 3 to 8 show modifications of the second embodiment.

FIG. 3 shows an embodiment using, as test piece 1, a continuous girder disposed between the two load plates 3a of the two load heads 3. The test piece 1 in this case represents only a relatively short section of the continuous girder to be examined. In this example, a measured supporting moment at the load head is the control variable. The bearing force is imposed on the test piece 1 by a hydraulic press 6, and is transmitted to the ground outside the test frame 2 via a bearing block 7. The microprocessor, though present, is omitted from FIGS. 3–8 for the sake of simplicity and clarity.

Figure 4:
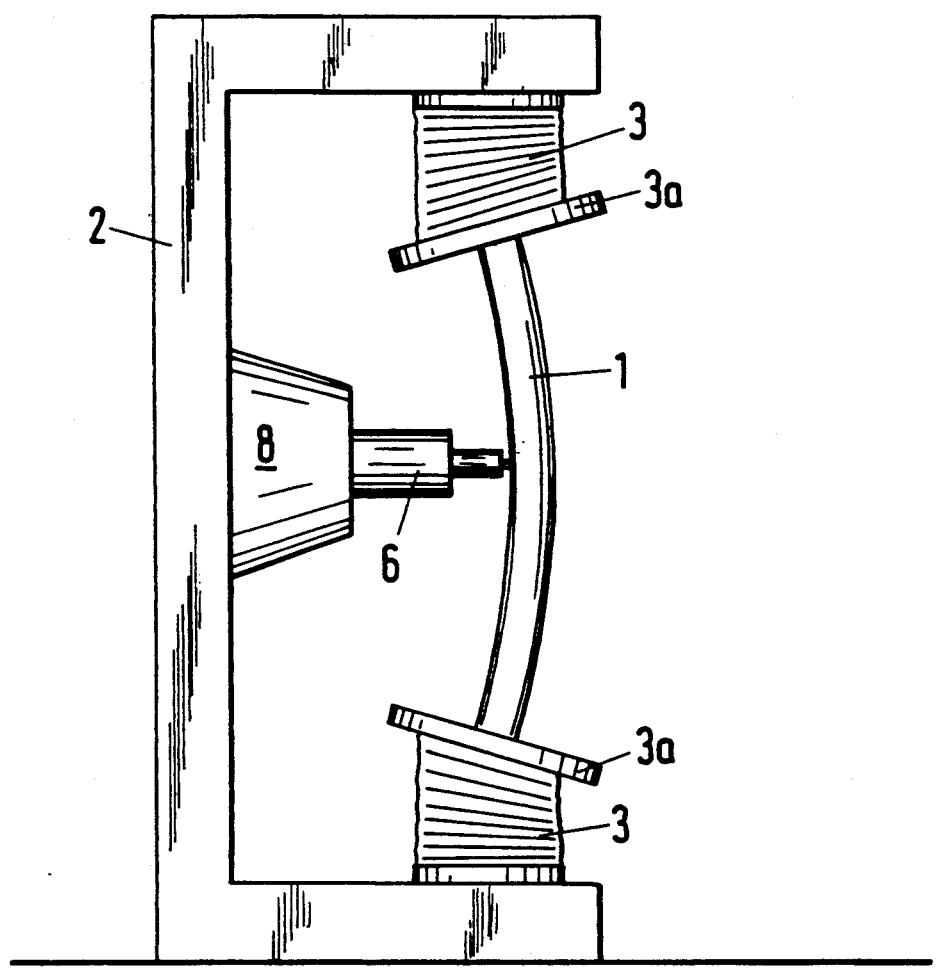

FIG. 4 shows a modification of the embodiment of FIG. 3 to the extent that the supporting force imposed by the hydraulic press 6 is introduced via a connecting piece 8 into the test frame 2, that is to say remains within the test apparatus.

Figure 5:
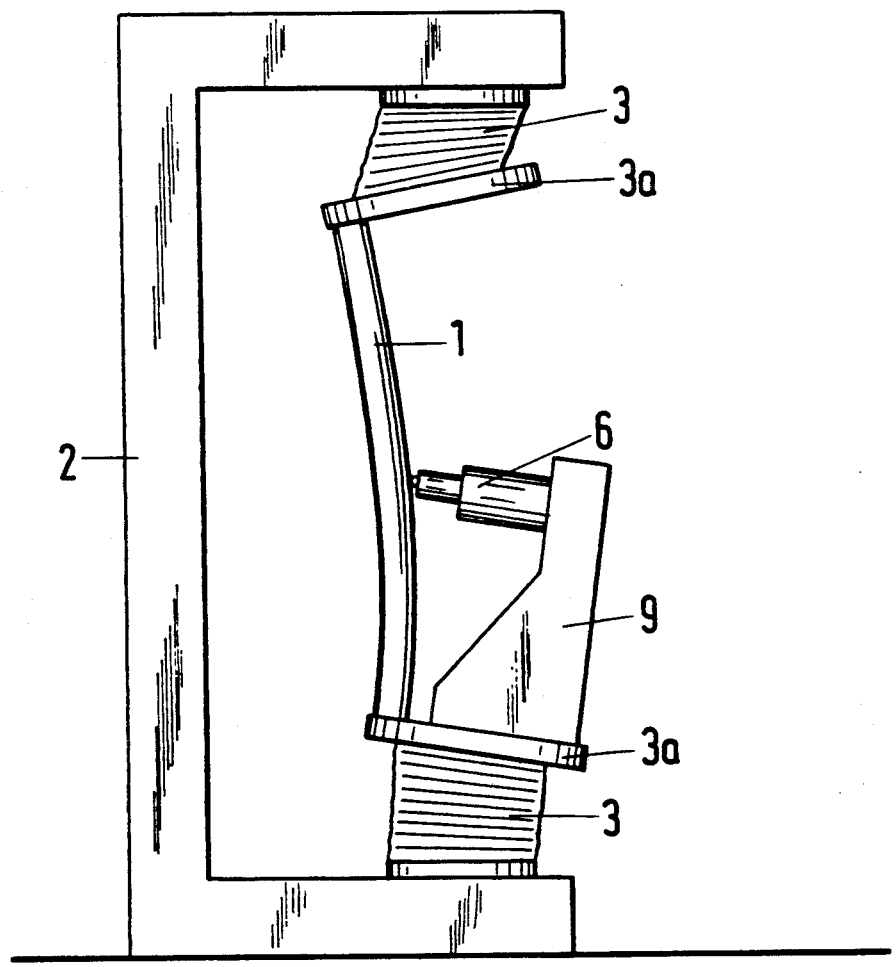

FIG. 5 illustrates an example of a test piece 1 in the form of a bracket support with additional loading by a horizontal force at half the support height. Here, the horizontal force is the additional control variable, which again is generated by a hydraulic press 6 and is introduced via a connecting piece 9 into the lower load plate 3a. Thus, the test frame 2 is not stressed by the horizontal force.

Figure 6:
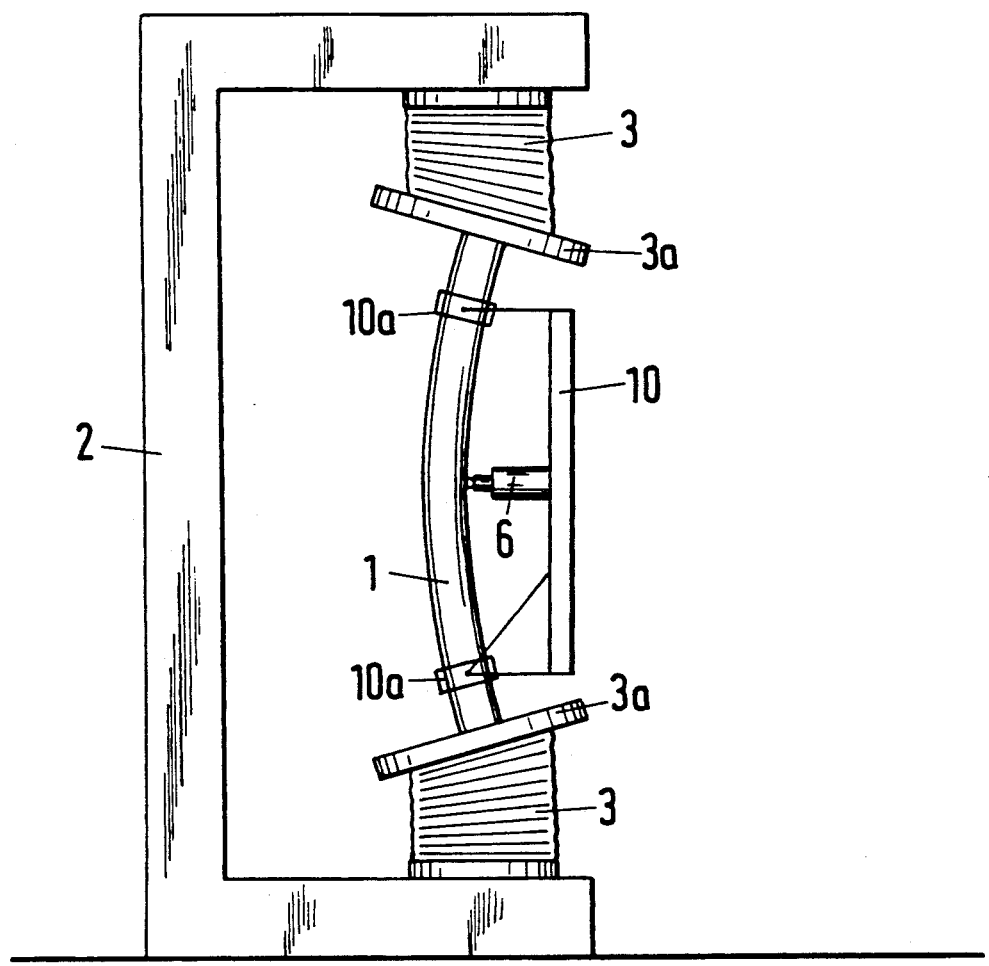

The embodiment of FIG. 6 differs from the illustrative embodiment according to FIG. 3 in that the supporting force (bearing force) applied by a hydraulic press 6 is transmitted to the test piece via a load-introducing yoke 10 with connecting pieces 10a for force introduction into the test piece 1. Consequently, the test apparatus is not stressed by the bearing force. The two load heads 3 have three degrees of freedom each.

Figure 7:
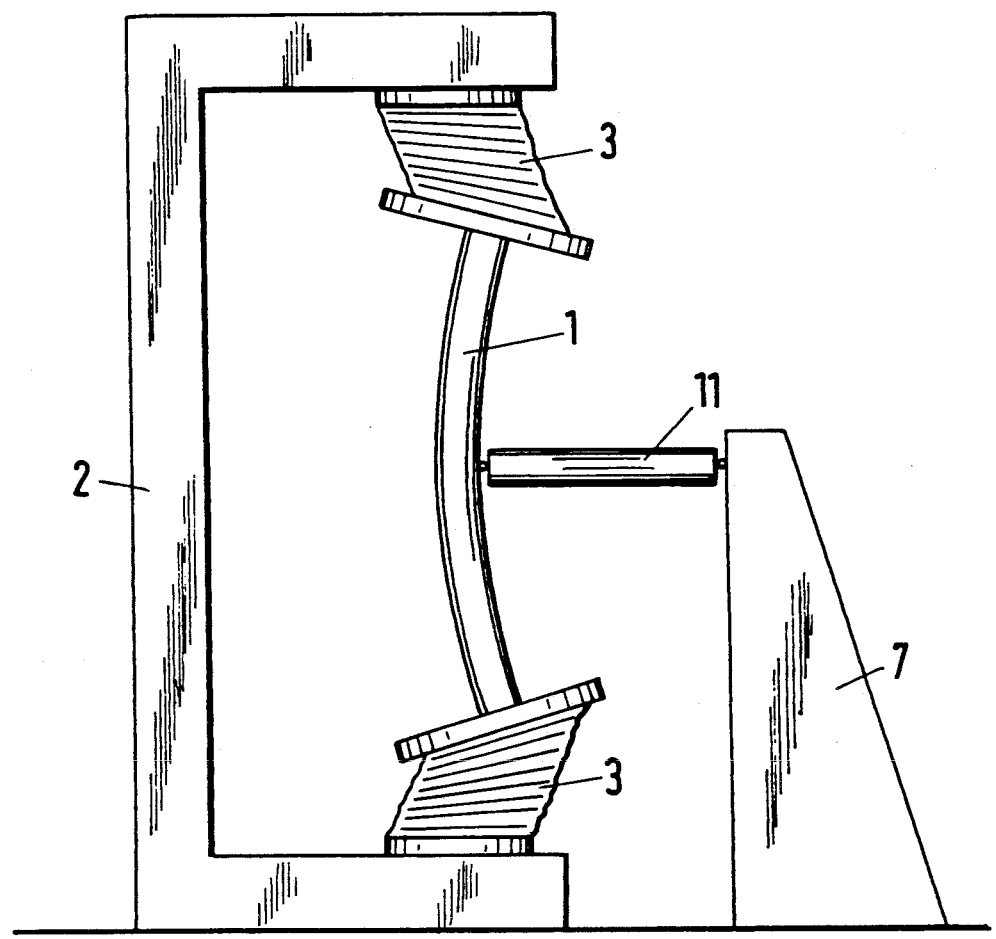

In the embodiment illustrated in FIG. 7, the test piece 1 is again a continuous girder. The supporting moment is the additional control variable. The bearing force is generated by using two load heads 3 to press the test piece 1 against a spacer 11, which transfers the force onto the bearing block 7, via which it is transmitted to the ground outside the test apparatus. The two load heads 3 have six degrees of freedom each.

Figure 8:
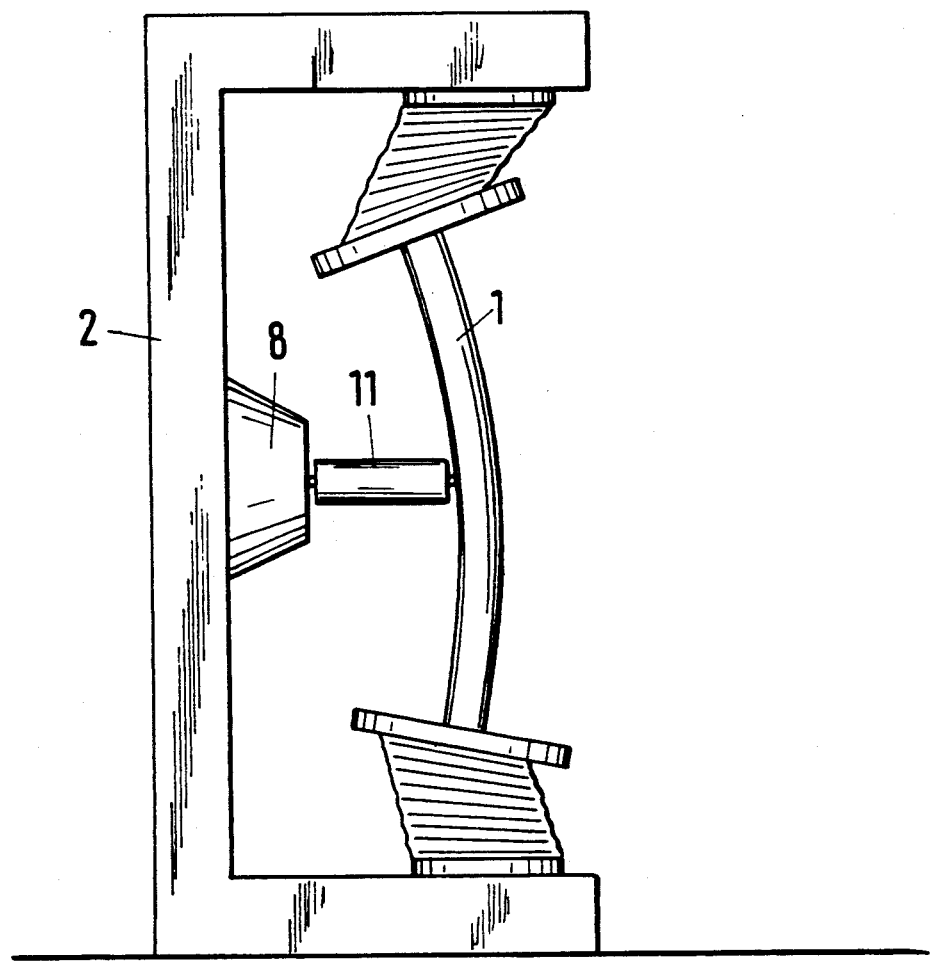

The apparatus of FIG. 8 corresponds to principle to the test apparatus according to FIG. 7, although the generated bearing force is led away via the spacer 11 into a connecting piece 8 which introduces force into the test frame 2. Thus, the bearing force remains within the test apparatus. Consequently, while it is assumed in the case of the prior art method that no forces (with the exception of forces of its own weight) act from the outside of the bar between its ends, that is on the bar itself, and also that no bearings are arranged, it is possible according to the invention to arrange supporting points on the test piece at which bearing forces can be taken (passively) or forces can be imposed (actively).

What is claimed is:

1. A method of testing a test piece having opposite ends, comprising the steps of:
   (A) connecting one end of said test piece to a plate of a test apparatus;
   (B) connecting the opposite end of said test piece to a first displaceable load head of said test apparatus, which load head is displaceable by actuating driving means;
   (C) displacing said load head by actuating said driving means;
   (D) determining the magnitude and direction of load forces and load moments applied to said first load head by said driving means, and measuring the actual magnitude and direction of displacement of said first load head in relation to a fixed plate, in order to set or vary boundary conditions of said test piece from the displacement of said first load head;
   (E) comparing actual values of said boundary conditions with freely programmable predetermined desired values of said boundary conditions to determine a test piece end value in the form of at least one at a displacement variable and a force variable to be used as a control variable for said driving means;
   (F) determining additional control variables for said driving means and substituting said additional control variables for at least one of said boundary conditions, wherein the functional dependencies of said additional control variables on said load head displacements all are known before said determining step or are identified during said determining step.

2. The method of claim 1, wherein the step of connecting one end of said test piece to a plate comprises the step of connecting said one end to a second displaceable load head.

3. The method of claim 2, further comprising the step of measuring a supporting force via one of said first and second load heads.

4. The method of claim 2, further comprising the step of connecting a third end of said test piece to a third displaceable load head.

5. The method of claim 2, wherein the steps of connecting said test piece to said first and second load heads comprise providing load heads with a total of six degrees of freedom.

6. The method of claim 2, wherein the steps of connecting said test piece to said first and second load heads comprise providing load heads with six degrees of freedom each.

7. The method of claim 1, wherein said step of determining additional control variables comprises the steps of imposing forces on said test area, measuring the imposed forces, and deriving said additional control variables from the measured force values.

8. The method of claim 7, wherein said imposed forces are transmitted outside of said test apparatus.

9. The method of claim 7, wherein said imposed forces are transmitted onto a test frame of said test apparatus.

10. The method of claim 7, wherein said imposed forces are transmitted onto said plate.

11. The method of claim 7, wherein said imposed forces are transmitted away from said test piece.

12. The method of claim 1, wherein the step of determining additional control variables is performed using values derived from measurements taken at a location intermediate said first and second ends.

13. The method of claim 12, wherein said taken forces are transmitted outside of said test apparatus.

14. The method of claim 12, wherein said taken forces are absorbed by a test frame of said test apparatus.

15. The method of claim 1, further comprising the step of directly measuring a supporting force.

16. An apparatus for testing a test piece having opposing ends, said apparatus comprising:
(A) a test frame;
(B) a plate supported on said test frame and connected to one end of said test piece;
(C) a first load head supported on said frame and connected to the opposite end of said test piece;
(D) driving means for spatially adjusting said first load head with respect to said plate, thereby applying a variable load to said test piece;
(E) means for determining the magnitude and direction of load forces applied to said first load head and for measuring the actual magnitude and direction of displacement of said first load head relative to said fixed plate in order to set or vary boundary conditions of said test piece from the displacement of said first load head;
(F) means for comparing actual values of said boundary conditions with freely programmable predetermined desired values of said boundary conditions to determine a test piece end value in the form of at least one of a displacement variable and a force variable, and for actuating said driving means using the determined test piece end value as a control variable; and
(G) means for determining additional control variables for said driving means and for substituting said additional control variables for at least one of said boundary conditions, wherein the functional dependencies of said additional control variables on said load head displacements are determined before said means for determining operates or by identifying said additional control variables when said means for determining operates.

17. The apparatus of claim 16, further comprising a second displaceable load head positioned between said plate and said test frame.

18. The apparatus of claim 17, wherein each of said first and second load heads have six degrees of freedom.

19. The apparatus of claim 17, wherein said first and second load heads have a combined total of six degrees of freedom.

20. The apparatus of claim 16, further comprising
means for imposing forces on an area of said test piece positioned intermediate said first and second ends and
means for measuring the imposed forces, wherein said means for deriving said additional control variables derives said additional control variables from the measured force values.

21. The apparatus of claim 16, further comprising
means for taking forces away from an area of said test piece positioned intermediate said first and second ends and means for measuring the taken forces, wherein said means for deriving said additional control variables derives said additional control variables from the measured force values.

22. The apparatus of claim 16, further comprising a third load head supporting a third end of said test piece.

* * * * *